시010633323B2

United States Patent
Sanuki et al.

(10) Patent No.: US 10,633,323 B2
(45) Date of Patent: Apr. 28, 2020

(54) METHOD OF PRODUCING ACID HALIDE SOLUTION AND METHOD OF PRODUCING MONOESTER COMPOUND

(71) Applicant: ZEON CORPORATION, Chiyoda-ku, Tokyo (JP)

(72) Inventors: Kanako Sanuki, Tokyo (JP); Kei Sakamoto, Tokyo (JP); Kumi Okuyama, Tokyo (JP); Hiroki Iwaki, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/069,994

(22) PCT Filed: Jan. 20, 2017

(86) PCT No.: PCT/JP2017/002024
§ 371 (c)(1),
(2) Date: Jul. 13, 2018

(87) PCT Pub. No.: WO2017/130871
PCT Pub. Date: Aug. 3, 2017

(65) Prior Publication Data
US 2019/0016662 A1 Jan. 17, 2019

(30) Foreign Application Priority Data

Jan. 26, 2016 (JP) ................................. 2016-012328

(51) Int. Cl.
| C07C 51/64 | (2006.01) |
| C07C 67/14 | (2006.01) |
| C07C 51/60 | (2006.01) |
| C07C 61/09 | (2006.01) |
| C07C 69/75 | (2006.01) |
| C07B 61/00 | (2006.01) |

(52) U.S. Cl.
CPC .............. *C07C 51/64* (2013.01); *C07C 51/60* (2013.01); *C07C 61/09* (2013.01); *C07C 67/14* (2013.01); *C07C 69/75* (2013.01); *C07B 61/00* (2013.01); *C07C 2601/14* (2017.05)

(58) Field of Classification Search
CPC ......... C07C 51/64; C07C 51/60; C07C 61/09; C07C 67/14
USPC ......................................................... 560/127
See application file for complete search history.

(56) References Cited

U.S. PATENT DOCUMENTS

| 5,663,432 A | 9/1997 | Villa et al. |
| 2015/0175564 A1 | 6/2015 | Sakamoto et al. |
| 2017/0158604 A1 | 6/2017 | Okuyama et al. |

FOREIGN PATENT DOCUMENTS

| EP | 2508504 A1 * | 10/2012 | ............. C07B 51/00 |
| JP | 111505234 A | 5/1999 | |
| JP | 2007314443 A | 12/2007 | |
| JP | 2013018714 A * | 1/2013 | |
| JP | 2013018714 A | 1/2013 | |
| WO | 2014010325 A1 | 1/2014 | |
| WO | 2016002816 A1 | 1/2016 | |
| WO | WO-2016002816 * | 1/2016 | ........... C07C 67/307 |

OTHER PUBLICATIONS

Kimura et al: "Novel Synthetic Method for the Vilsmeier-Haack Reagent and Green Routes to Acid Chlorides, Alkyl Formates, and Alkyl Chlorides", International Journal of Organic Chemistry, vol. 3, No. 3, pp. 1-7. (Abstract) (Year: 2013).*
Jul. 31, 2018, International Preliminary Report on Patentability issued in the International Patent Application No. PCT/JP2017/002024.
Apr. 25, 2017, International Search Report issued in the International Patent Application No. PCT/JP2017/002024.
Kenneth A. Burdett, An Improved Acid Chloride Preparation via Phase Transfer Catalysis, Synthesis, Jun. 1991, pp. 441-442, No. 6, Thieme Medical Publishers, Inc., New York.
Jun. 11, 2019, the Extended European Search Report issued by the European Patent Office in the corresponding European Patent Application No. 177441011.
Yoshikazu Kimura et al., Novel Synthetic Method for the Vilsmeier-Haack Reagent and Green Routes to Acid Chlorides, Alkyl Formates, and Alkyl Chlorides, International Journal of Organic Chemistry, 2013, pp. 1-7, vol. 3, No. 3.

* cited by examiner

*Primary Examiner* — Deborah D Carr
(74) *Attorney, Agent, or Firm* — Kenja IP Law PC

(57) ABSTRACT

Provided is a method of producing an acid halide solution that is useful in production of a polymerizable liquid-crystal compound. The method of producing an acid halide solution includes: a first step of reacting a specific dicarboxylic acid compound with a halogenating agent in a water-immiscible organic solvent in the presence of at least 1.1 equivalents and not more than 3.0 equivalents of an activator relative to the dicarboxylic acid compound to obtain a reaction liquid including a solution that contains an acid halide compound and an oily liquid that is immiscible with the solution containing the acid halide compound; and a second step of removing the oily liquid from the reaction liquid obtained in the first step to obtain a purified liquid containing the acid halide compound.

15 Claims, No Drawings

METHOD OF PRODUCING ACID HALIDE SOLUTION AND METHOD OF PRODUCING MONOESTER COMPOUND

TECHNICAL FIELD

The present disclosure relates to a method of producing an acid halide solution and a method of producing a monoester compound using the acid halide solution that are useful in production of a polymerizable liquid-crystal compound.

BACKGROUND

Monoester compounds of cycloalkane dicarboxylic acids are compounds that are useful as production intermediates for liquid-crystal materials, electron transport materials, and the like (for example, refer to PTL 1). These monoester compounds are normally synthesized through reaction of a dicarboxylic acid chloride and a hydroxy compound.

One known method of producing a dicarboxylic acid chloride is a method (acid halide method) in which a chlorinating agent such as thionyl chloride is caused to act on a dicarboxylic acid compound in the presence of a reaction catalyst (herein, also referred to as an "activator") such as N,N-dimethylformamide, triethylamine, or a tetraalkylammonium salt.

For example, PTL 2 describes a method of producing 5-amino-2,4,6-triiodoisophthalic acid dichloride by reacting thionyl chloride with 5-amino-2,4,6-triiodoisophthalic acid in the presence of a tetraalkylammonium salt.

Moreover, PTL 3 describes a method of producing an ester group-containing tetracarboxylic dianhydride having a specific structure by the acid halide method. Furthermore, PTL 3 explains that when reacting thionyl chloride with a dicarboxylic acid, N,N-dimethylformamide or pyridine may be added to the reaction system as a catalyst.

Also, NPL 1 describes a method of producing a dichloride of a dicarboxylic acid by reacting thionyl chloride with a dicarboxylic acid having a specific structure in the presence of benzyltriethylammonium chloride.

CITATION LIST

Patent Literature

PTL 1: WO 2014/010325 A1
PTL 2: JP H11-505234 A
PTL 3: JP 2007-314443 A

Non-Patent Literature

NPL 1: A. Burdett, Synthesis, 1991, 441

SUMMARY

Technical Problem

In the case of production of a monoester compound by reacting a dicarboxylic acid chloride obtained by the acid halide method with a hydroxy compound, the dicarboxylic acid chloride serving as a raw material is isolated for use. Specifically, the dicarboxylic acid chloride obtained by the acid halide method is used in production of the monoester compound after removing solvent and low boiling point substances from a reaction liquid obtained through reaction of a dicarboxylic acid compound with a chlorinating agent such as thionyl chloride, and then isolating the dicarboxylic acid chloride from the residue by recrystallization or the like. This is performed to completely remove acid components such as $SO_2$, HCl, and $SOCl_2$ originating from the chlorinating agent prior to the subsequent esterification reaction because the reaction yield of the esterification reaction significantly decreases if such acid components remain.

Although a purification method such as recrystallization can be used in production of a target on a small scale, purification methods such as recrystallization are difficult to implement for production on an industrial scale and are not considered to be industrially advantageous production methods.

The present disclosure is made in light of the circumstances set forth above and an objective thereof is to provide a method of producing an acid halide solution and a method of producing a monoester compound using the acid halide solution that enable industrially advantageous production of a polymerizable liquid-crystal compound.

Solution to Problem

With the aim of solving the problems set forth above, the inventors conducted a diligent investigation in relation to an industrial production method for producing a dicarboxylic acid chloride by reacting thionyl chloride with a dicarboxylic acid compound in a water-immiscible organic solvent in the presence of an activator and then producing a monoester compound using the resultant dicarboxylic acid chloride. The inventors attempted to use a method in which a reaction liquid containing a produced dicarboxylic acid chloride was concentrated by distillation without reaching dryness and then an esterification reaction was carried out in this state.

As a result, the inventors realized that there are cases in which a dicarboxylic acid chloride cannot be efficiently produced if the amount of activator that is used is too small. On the other hand, although there is no problem in terms of production of a dicarboxylic acid chloride when a comparatively large amount of activator is used, the inventors found that the resultant reaction liquid includes an oily liquid that is immiscible with a water-immiscible organic solvent, and when such a reaction liquid is used in an esterification reaction in this form, there is a significant decrease in the conversion rate from dicarboxylic acid chloride to ester.

The present disclosure was completed based on these findings.

Thus, the present disclosure provides the following methods of producing an acid halide solution (1) to (9) and the following methods of producing a monoester compound (10) to (14).

(1) A method of producing an acid halide solution comprising:

a first step of reacting a dicarboxylic acid compound of formula (I), shown below,

where n is 0 or 1, with a halogenating agent in a water-immiscible organic solvent in the presence of at least 1.1 equivalents and not more than 3.0 equivalents of an activator relative to the dicarboxylic acid compound of formula (I) to obtain a reaction liquid including a solution that contains an acid halide compound of formula (II), shown below,

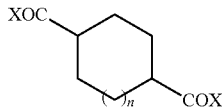

where n is 0 or 1 and X is a halogen atom, and an oily liquid that is immiscible with the solution; and a second step of removing the oily liquid from the reaction liquid obtained in the first step to obtain a purified liquid containing the acid halide compound of formula (II).

(2) The method of producing an acid halide solution according to (1), further comprising a third step of, after the second step, concentrating the purified liquid obtained in the second step.

(3) The method of producing an acid halide solution according to (1) or (2), wherein the dicarboxylic acid compound of formula (I) is a compound of formula (I-a), shown below,

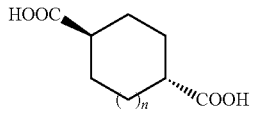

where n is 0 or 1.

(4) The method of producing an acid halide solution according to any one of (1) to (3), wherein the activator is a nitrogen atom-containing polar aprotic solvent or a tetraalkylammonium salt of formula (III), shown below, $$R^1R^2R^3R^4N^+A^-$$ (III)

where $A^-$ is a halide ion or $R^5SO_3^-$ in which $R^5$ is a methyl group, a phenyl group, or a 4-methylphenyl group, and $R^1$, $R^2$, $R^3$, and $R^4$ are each, independently of one another, a substituted or unsubstituted alkyl group with a proviso that $R^1$, $R^2$, $R^3$, and $R^4$ have a total number of carbon atoms of at least 4 and not more than 100.

(5) The method of producing an acid halide solution according to (4), wherein the nitrogen atom-containing polar aprotic solvent is an amide solvent.

(6) The method of producing an acid halide solution according to (5), wherein the amide solvent is at least one selected from the group consisting of N,N-dimethylformamide, N,N-dimethylacetamide, N-methylpyrrolidone, and 1,3-dimethyl-2-imidazolidinone.

(7) The method of producing an acid halide solution according to (4), wherein the tetraalkylammonium salt of formula (III) is at least one selected from the group consisting of benzyltriethylammonium chloride, methyltrioctylammonium chloride, tetrabutylammonium chloride, and benzyltrimethylammonium chloride.

(8) The method of producing an acid halide solution according to any one of (1) to (7), wherein the halogenating agent is at least one selected from the group consisting of thionyl chloride, oxalyl chloride, sulfuryl chloride, phosphoryl chloride, phosphorus trichloride, and phosphorus pentachloride.

(9) The method of producing an acid halide solution according to any one of (1) to (8), wherein the acid halide compound of formula (II) is a dicarboxylic acid chloride of formula (II-1), shown below,

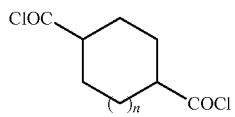

where n is 0 or 1.

(10) A method of producing a monoester compound of formula (V), shown below,

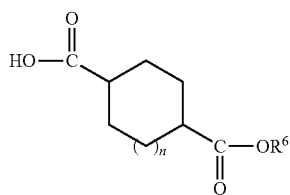

where $R^6$ is an organic group and n is 0 or 1, comprising a fourth step of adding a hydroxy compound of formula (IV): $R^6OH$, where $R^6$ is the same as above, and a base to an acid halide solution obtained by the method of producing an acid halide solution according to any one of (1) to (9).

(11) The method of producing a monoester compound according to (10), wherein the hydroxy compound of formula (IV) is a compound of formula (IV-1), shown below,

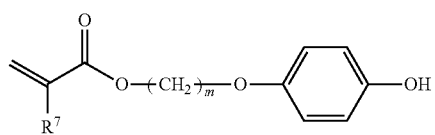

where $R^7$ is a hydrogen atom, a methyl group, or a chlorine atom and m is an integer of at least 1 and not more than 20.

(12) The method of producing a monoester compound according to (10) or (11), further comprising a fifth step of, after the fourth step, washing a reaction liquid obtained through the fourth step with a weakly acidic buffer solution.

(13) The method of producing a monoester compound according to (12), wherein the weakly acidic buffer solution is an aqueous solution having a pH of at least 5.0 and not higher than 6.0.

(14) The method of producing a monoester compound according to (12) or (13), wherein the weakly acidic buffer solution is either or both of an aqueous solution of a mixture of acetic acid and sodium acetate and an aqueous solution of a mixture of potassium hydrogen phthalate and sodium hydroxide.

Advantageous Effect

The present disclosure provides a method of producing an acid halide solution and a method of producing a monoester compound using the acid halide solution that are useful in production of a polymerizable liquid-crystal compound.

DETAILED DESCRIPTION

The following provides a detailed description of the present disclosure split into sections relating to 1) a method of producing an acid halide solution and 2) a method of producing a monoester compound.

1) Method of Producing Acid Halide Solution

A presently disclosed method of producing an acid halide solution includes: a first step of reacting a dicarboxylic acid compound of the previously shown formula (I) (hereinafter, also referred to as "dicarboxylic acid compound (I)") with a halogenating agent in a water-immiscible organic solvent in the presence of at least 1.1 equivalents and not more than 3.0 equivalents of an activator relative to the dicarboxylic acid compound (I) to obtain a reaction liquid including a solution that contains an acid halide compound of the previously shown formula (II) (hereinafter, also referred to as "acid halide compound (II)") and an oily liquid that is immiscible with the solution; and a second step of removing the oily liquid from the reaction liquid obtained in the first step to obtain a purified liquid containing the acid halide compound (II).

In this disclosure, the term "equivalents" refers to "molar equivalents".

(First Step)

The first step is a step of reacting a dicarboxylic acid compound (I) with a halogenating agent in a water-immiscible organic solvent in the presence of at least 1.1 equivalents and not more than 3.0 equivalents of an activator relative to the dicarboxylic acid compound (I) to obtain a reaction liquid including a solution that contains an acid halide compound (II) and an oily liquid that is immiscible with the solution.

(Water-Immiscible Organic Solvent)

The water-immiscible organic solvent used in the present disclosure may, without any specific limitations, be any organic solvent in which the dicarboxylic acid compound (I) and the acid halide compound (II) corresponding to the dicarboxylic acid compound (I) dissolve and that is immiscible with water. For example, an organic solvent that has a solubility of 10 g/L or less with respect to water at 25° C. may be used as an organic solvent that is immiscible with water.

Specific examples of water-immiscible organic solvents that may be used include ester solvents such as ethyl acetate, propyl acetate, and butyl acetate; halogenated hydrocarbon solvents such as dichloromethane, 1,2-dichloroethane, chloroform, carbon tetrachloride, chlorobenzene, and o-dichlorobenzene; ether solvents such as diethyl ether, dibutyl ether, diisopropyl ether, ethylene glycol dimethyl ether, cyclopentyl methyl ether, methyl t-butyl ether, and 1,2-dimethoxyethane; chain aliphatic hydrocarbon solvents such as n-pentane, n-hexane, and n-heptane; aromatic hydrocarbon solvents such as benzene, toluene, and xylene; alicyclic hydrocarbon solvents such as cyclopentane and cyclohexane; and ketone solvents such as 2-butanone.

One of these solvents may be used individually, or two or more of these solvents may be used in combination.

Of these solvents, halogenated hydrocarbon solvents, ether solvents, aromatic hydrocarbon solvents, and alicyclic hydrocarbon solvents are preferable, and cyclopentyl methyl ether, chloroform, cyclohexane, and toluene are more preferable.

In particular, organic solvents having a Hildebrand solubility parameter of at least 14.0 $MPa^{1/2}$ and not more than 22.0 $MPa^{1/2}$ are preferable as the water-immiscible organic solvent. The Hildebrand solubility parameter is a value ($\delta$) that provides a numerical estimate of the degree of interaction between materials as defined by regular solution theory introduced by Hildebrand.

The use of an organic solvent such as described above facilitates operation in a subsequent washing step and enables the efficient acquisition of a target monoester compound.

Specific examples of preferable water-immiscible organic solvents include ether solvents such as cyclopentyl methyl ether (Hildebrand solubility parameter ($\delta$): 17.2 $MPa^{1/2}$), methyl t-butyl ether ($\delta$: 15.6 $MPa^{1/2}$), diethyl ether ($\delta$: 15.1 $MPa^{1/2}$), dibutyl ether ($\delta$: 14.9 $MPa^{1/2}$), diisopropyl ether ($\delta$: 14.1 $MPa^{1/2}$), and 1,2-dimethoxyethane ($\delta$: 19.2 $MPa^{1/2}$); halogenated hydrocarbon solvents such as chloroform ($\delta$: 19.0 $MPa^{1/2}$); ester solvents such as ethyl acetate ($\delta$: 18.6 $MPa^{1/2}$); aromatic hydrocarbon solvents such as toluene ($\delta$: 18.2 $MPa^{1/2}$); alicyclic hydrocarbon solvents such as cyclohexane ($\delta$: 16.7 $MPa^{1/2}$); ketone solvents such as 2-butanone ($\delta$: 19.0 $MPa^{1/2}$); and mixed solvents of any of these solvents. Note that in the case of a mixed solvent, the solubility parameter of the mixed solvent can be calculated by the addition rule.

(Dicarboxylic Acid Compound (I))

The dicarboxylic acid compound (I) used in the present disclosure is a dicarboxylic acid of formula (I). In formula (I), n is 0 or 1, and is preferably 1.

Specific examples of the dicarboxylic acid compound (I) include 1,3-cyclopentanedicarboxylic acid and 1,4-cyclohexanedicarboxylic acid. Of these examples, 1,4-cyclohexanedicarboxylic acid is preferable from a viewpoint of usefulness as a production raw material for a polymerizable liquid-crystal compound.

As illustrated by the following formulae (I-1) and (I-2), cis and trans stereoisomers of the dicarboxylic acid compound (I) exist. In the present disclosure, the cis isomer, the trans isomer, or a cis-trans isomer mixture (racemate) may be used. Of these isomers, the trans isomer of formula (I-1) is preferable from a viewpoint of usefulness as a production intermediate for a polymerizable liquid-crystal compound or the like.

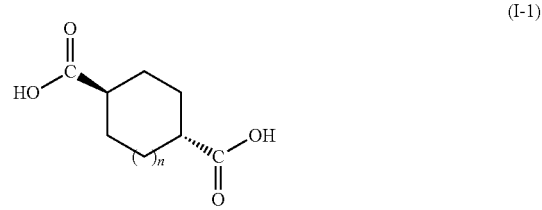

(I-1)

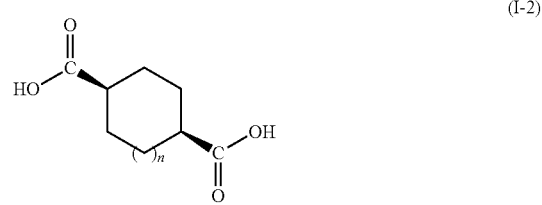

(I-2)

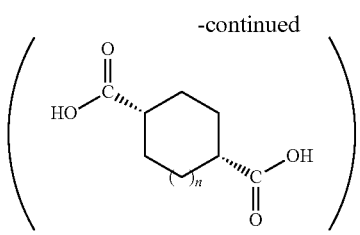

(Activator)

The activator used in the present disclosure is a compound that promotes a reaction of the dicarboxylic acid compound (I) and the halogenating agent.

By using the activator, the target acid halide compound (II) can be obtained through a lower reaction temperature, in a shorter time, and with a better yield.

Examples of activators that may be used include nitrogen atom-containing polar aprotic solvents and tetraalkylammonium salts of the previously shown formula (III) (hereinafter, also referred to as "tetraalkylammonium salts (III)").

Examples of nitrogen atom-containing polar aprotic solvents that may be used include amide solvents such as N,N-dimethylformamide, N,N-dimethylacetamide, N-methylpyrrolidone, and 1,3-dimethyl-2-imidazolidinone; amine solvents such as N,N,N',N'-tetramethylethylenediamine and N,N-dimethylaniline; and nitrile solvents such as acetonitrile and propionitrile.

One of these solvents may be used individually, or two or more of these solvents may be used in combination.

Of these nitrogen atom-containing polar aprotic solvents, amide solvents are preferable because they enable acquisition of the target acid halide compound (II) with a good yield.

In the present disclosure, the "nitrogen atom-containing polar aprotic solvent" is miscible with water and may, for example, have a solubility of more than 10 g/L with respect to water at 25° C. Accordingly, organic solvents that correspond to the previously described water-immiscible organic solvent are not included among nitrogen atom-containing polar aprotic solvents.

The tetraalkylammonium salt (III) is a tetraalkylammonium salt of formula (III).

In formula (III), $A^-$ is a halide ion such as a chloride ion or a bromide ion; or a sulfonate ion having a formula: $R^5SO_3^-$, where $R^5$ is a methyl group, a phenyl group, or a 4-methylphenyl group.

$A^-$ is preferably a halide ion, and particularly preferably a chloride ion from a viewpoint of versatility.

$R^1$, $R^2$, $R^3$, and $R^4$ in formula (III) are each, independently of one another, a substituted or unsubstituted alkyl group.

The alkyl group of the substituted or unsubstituted alkyl group of $R^1$, $R^2$, $R^3$, and $R^4$ may be an alkyl group having a carbon number of at least 1 and not more than 30, preferably an alkyl group having a carbon number of at least 1 and not more than 20, and more preferably an alkyl group having a carbon number of at least 1 and not more than 18. The alkyl group of $R^1$, $R^2$, $R^3$, and $R^4$ may have a linear structure or a branched structure.

Specific examples of the alkyl group of the substituted or unsubstituted alkyl group of $R^1$, $R^2$, $R^3$, and $R^4$ include a methyl group, an ethyl group, an n-propyl group, an isopropyl group, an n-butyl group, an isobutyl group, a sec-butyl group, a t-butyl group, an n-pentyl group, an isoamyl group, an n-hexyl group, an n-heptyl group, an n-octyl group, an n-nonyl group, an n-decyl group, an n-undecyl group, an n-dodecyl group, and a cetyl group.

The total number of carbon atoms of $R^1$, $R^2$, $R^3$, and $R^4$ is at least 4 and not more than 100, preferably at least 4 and not more than 80, more preferably at least 4 and not more than 50, and particularly preferably at least 4 and not more than 30.

Examples of substituents that may be included in the alkyl group of $R^1$, $R^2$, $R^3$, and $R^4$ include, without any specific limitations, groups that are inert with respect to the reaction. Specific examples include alkoxy groups having a carbon number of at least 1 and not more than 10 such as a methoxy group, an ethoxy group, a propoxy group, and a butoxy group; and substituted or unsubstituted phenyl groups such as a phenyl group, a 2-chlorophenyl group, a 4-methylphenyl group, and a phenethyl group.

Specific examples of substituted alkyl groups for $R^1$, $R^2$, $R^3$, and $R^4$ include, but are not limited to, a 2-methoxyethyl group, a 3-methoxypropyl group, a benzyl group, a 4-methylbenzyl group, and a phenethyl group.

Specific examples of preferable tetraalkylammonium salts (III) include benzyltriethylammonium chloride, methyltrioctylammonium chloride, tetrabutylammonium chloride, and benzyltrimethylammonium chloride.

One tetraalkylammonium salt (III) may be used individually, or two or more tetraalkylammonium salts (III) may be used in combination.

(Halogenating Agent)

No specific limitations are placed on the halogenating agent used in the present disclosure so long as the halogenating agent enables conversion of the dicarboxylic acid compound (I) to the corresponding acid halide compound (II).

Examples of halogenating agents that may be used include chlorinating agents such as thionyl chloride ($SOCl_2$), oxalyl chloride (($COCl)_2$), sulfuryl chloride ($SO_2Cl_2$), phosphoryl chloride ($POCl_3$), phosphorus trichloride ($PCl_3$), and phosphorus pentachloride ($PCl_5$); and brominating agents such as thionyl bromide ($SOBr_2$), boron tribromide ($BBr_3$), and bromine ($Br_2$).

One of these halogenating agents may be used individually, or two or more of these halogenating agents may be used in combination.

Of these halogenating agents, at least one selected from the group consisting of thionyl chloride, oxalyl chloride, sulfuryl chloride, phosphoryl chloride, phosphorus trichloride, and phosphorus pentachloride is preferable from a viewpoint of versatility.

(Reaction of Dicarboxylic Acid Compound (I) and Halogenating Agent)

In the first step, the dicarboxylic acid compound (I) is reacted with the halogenating agent in the water-immiscible organic solvent in the presence of at least 1.1 equivalents and not more than 3.0 equivalents of the activator relative to the dicarboxylic acid compound (I).

In the presently disclosed production method, at least 1.1 equivalents and not more than 3.0 equivalents of the activator are used relative to the dicarboxylic acid compound (I). If the amount of the activator is less than 1.1 equivalents, the halogenation reaction has a low conversion rate and the reaction may not be completed, and thus the yield tends to decrease. On the other hand, if the activator is added in an amount exceeding 3.0 equivalents, it is difficult to obtain an effect that is commensurate with the additive amount of activator. From these viewpoints, the amount of the activator is preferably at least 1.1 equivalents and not more than 2.8 equivalents relative to the dicarboxylic acid compound (I).

So long as this condition relating to the additive amount of the activator is satisfied, no specific limitations are placed on the method by which the dicarboxylic acid compound (I) and the halogenating agent are reacted. For example, a method may be adopted in which a specific amount of the activator is added into a water-immiscible organic solvent solution of the dicarboxylic acid compound (I), a specific amount of the halogenating agent is subsequently added, and then the entire contents are stirred.

Although no specific limitations are placed on the amount of the water-immiscible organic solvent that is used in the reaction of the dicarboxylic acid compound (I) and the halogenating agent, the amount of the water-immiscible organic solvent per 1 g of the dicarboxylic acid compound (I) is normally at least 0.1 g and not more than 100 g, and preferably at least 0.5 g and not more than 50 g. Moreover, although no specific limitations are placed on the amount of the halogenating agent that is used, the amount of the halogenating agent per 1 mol of the dicarboxylic acid compound (I) is normally at least 2 mol and not more than 5 mol, and preferably at least 2 mol and not more than 3 mol.

The reaction temperature is normally at least 0° C. and not higher than 100° C., and preferably at least 0° C. and not higher than 50° C., but is not specifically limited thereto.

Moreover, the reaction time is normally from a few minutes to 8 hours but is dependent on the type of substrate, scale of reaction, and so forth.

In the presently disclosed production method, a reaction liquid including a solution that contains an acid halide compound (II) and an oily liquid that is immiscible with the solution containing the acid halide compound (II) is obtained through reaction of the dicarboxylic acid compound (I) and the halogenating agent.

The acid halide compound (II) is the target of this reaction.

Among acid halide compounds (II), a dicarboxylic acid chloride of formula (II-1), shown below,

(in formula (II-1), n is 0 or 1) is preferable from a viewpoint of usefulness as a production intermediate for a polymerizable liquid-crystal compound or the like.

On the other hand, the oily liquid is a by-product of the reaction of the dicarboxylic acid compound (I) and the halogenating agent. The amount of the oily liquid that is produced tends to increase when the reaction is carried out in the presence of a large amount of activator.

In the presently disclosed production method, the phrase "reaction liquid including a solution that contains an acid halide compound (II) and an oily liquid that is immiscible with the solution" means that, at least under the conditions during implementation of the subsequently described second step, the reaction liquid separates into a solution containing an acid halide compound (II) and an oily liquid. In other words, even in a case in which, for example, the oily liquid is miscible with the solution containing the acid halide compound (II) when the temperature is $T_1$, so long as the oily liquid separates from the solution containing the acid halide compound (II) when the temperature is $T_2$, the subsequent second step can be implemented by setting the temperature as $T_2$.

Thus, the term "immiscible" as used in relation to the presently disclosed production method does not mean that "the oily liquid is immiscible with the solution containing the acid halide compound (II) under all conditions", but instead means that "the oily liquid is immiscible with the solution containing the acid halide compound (II) under conditions during implementation of the second step".

From a viewpoint of efficiently carrying out the second step, it is preferable that there is a temperature condition within a range of −5° C. to 30° C. under which the oily liquid is immiscible with the solution containing the acid halide compound (II). Furthermore, it is more preferable that the oily liquid is immiscible with the solution containing the acid halide compound (II) in a temperature region (i.e., under all temperature conditions) within a range of −5° C. to 30° C.

(Second Step)

The second step is a step in which the oily liquid is removed from the reaction liquid obtained in the first step to obtain a purified liquid containing the acid halide compound (II).

If the reaction liquid is subjected to an esterification reaction in a state containing the oily liquid or a concentrated liquid thereof is subjected to an esterification reaction, the yield of the esterification reaction tends to decrease. Therefore, the second step is included in the presently disclosed production method so as to remove the oily liquid from the reaction liquid and prepare a purified liquid containing the acid halide compound (II).

No specific limitations are placed on the method by which the oily liquid is removed from the reaction liquid. Normally, the oily liquid can be easily removed from the reaction liquid by, for example, performing liquid separation since the oily liquid is immiscible with the water-immiscible organic solvent.

The liquid separation is preferably implemented at at least −5° C. and not higher than 30° C.

Moreover, solvent may be added in the liquid separation so long as the reaction liquid maintains a two layer state.

Note that the purified liquid containing the acid halide compound (II) that is obtained in the second step may be used in this form as an acid halide solution in production of a monoester compound described further below.

(Third Step)

Although the purified liquid obtained as described above in the second step can be used in production of a monoester compound in this form, it is preferable that the purified liquid is concentrated to remove some of the solvent in the purified liquid. In other words, the presently disclosed production method preferably further includes a third step of concentrating the purified liquid obtained in the second step.

Through inclusion of the third step, the concentration of the acid halide compound (II) increases, and a purified liquid that is more suitable for use as a raw material solution in an esterification reaction is obtained. Moreover, by performing the third step, by-products that are not completely removed in the second step (for example, acid components such as $SO_2$, HCl, and $SOCl_2$ that originate from the halogenating agent) can be removed. In other words, through inclusion of the third step, acid components originating from the halogenating agent (acid components such as $SO_2$, HCl, and $SOCl_2$) that remain in the reaction system can be removed.

In the present disclosure, "concentrate" does not refer to complete removal of solvent from the purified liquid containing the acid halide compound (II) that is obtained in the second step. The purified liquid is normally concentrated until the amount of solvent in the purified liquid, as a mass ratio, is at least 1/10 and not more than 4/5 of the initial amount of solvent (charged amount), and preferably at least 1/10 and not more than 1/2 of the initial amount of solvent.

Although no specific limitations are placed on the method of concentration, an evaporation concentration method using an evaporation concentrating apparatus such as an evaporator may, for example, be adopted.

The concentrating operation may be carried out under normal pressure (approximately 0.1 MPa) or under vacuum. It is preferable that the operation is carried out under vacuum from a viewpoint of efficiency carrying out the concentrating operation. In a case in which the concentrating is carried out under vacuum, the degree of vacuum is normally at least 10 mmHg and not more than 500 mmHg.

In this manner, a concentrated liquid of the purified liquid containing the acid halide compound (II) (i.e., an acid halide solution) can be obtained.

The obtained acid halide solution is useful as a raw material solution in production of a monoester compound through an esterification reaction with a hydroxy compound as described below.

2) Method of Producing Monoester Compound

A presently disclosed method of producing a monoester compound includes a fourth step of adding a hydroxy compound of formula (IV): $R^6OH$ (in formula (IV), $R^6$ is an organic group) (hereinafter, also referred to as "hydroxy compound (IV)") and a base to the acid halide solution obtained through the presently disclosed method of producing an acid halide solution set forth above.

The following illustrates an example of a reaction scheme of the presently disclosed method of producing a monoester compound. Note that although the following illustrates a case in which X of the acid halide compound (II) contained in the acid halide solution is a chlorine atom and thus the acid halide compound (II) is a dicarboxylic acid chloride (II-1), the present disclosure is not limited to the following example.

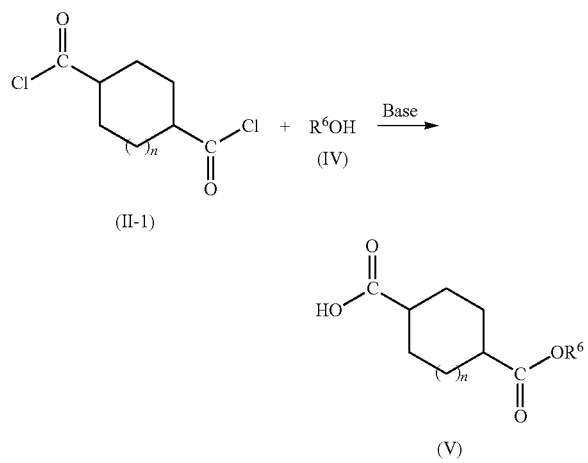

Specifically, the presently disclosed method of producing a monoester compound is a method in which an acid halide compound of formula (II) (dicarboxylic acid chloride (II-1) in the above example) and a hydroxy compound of formula (IV) are reacted to obtain a monoester compound of formula (V) (hereinafter, also referred to as "monoester compound (V)"). Note that the unreacted acid halide part (acid chloride part on the left-hand side in the above example) is converted to a carboxyl group by hydrolysis in a treatment process of the obtained reaction liquid.

In formula (V), n is 0 or 1, and is preferably 1. The monoester compound (V) is a compound resulting from monoesterification of the acid halide compound (II). Accordingly, n in formula (II) and n in formula (V) are normally the same.

In formulae (IV) and (V), $R^6$ is an organic group. The $R^6$ organic group is a group that bonds through a carbon atom to an oxygen atom of a hydroxy group or the like.

The carbon number of the $R^6$ organic group is not specifically limited, but is preferably at least 1 and not more than 30.

Examples of the organic group include substituted or unsubstituted aliphatic hydrocarbon groups such as substituted or unsubstituted alkyl groups having a carbon number of at least 1 and not more than 30, substituted or unsubstituted alkenyl groups having a carbon number of at least 2 and not more than 30, substituted or unsubstituted alkynyl groups having a carbon number of at least 2 and not more than 30, and substituted or unsubstituted cycloalkyl groups having a carbon number of at least 3 and not more than 30; substituted or unsubstituted aromatic hydrocarbon groups having a carbon number of at least 6 and not more than 30; and substituted or unsubstituted aromatic heterocyclic groups having a carbon number of at least 1 and not more than 30.

The hydroxy compound (IV) used in the present disclosure may be an alcohol compound for which $R^6$ is a substituted or unsubstituted aliphatic hydrocarbon group, or may be a phenolic compound for which $R^6$ is a substituted or unsubstituted aromatic hydrocarbon group having a carbon number of at least 6 and not more than 30, or a substituted or unsubstituted aromatic heterocyclic group having a carbon number of at least 1 and not more than 30. In the present disclosure, the hydroxy compound (IV) is preferably a phenolic compound, more preferably a phenolic compound for which $R^6$ is a substituted or unsubstituted aromatic hydrocarbon group having a carbon number of at least 6 and not more than 30, and particularly preferably a compound of formula (IV-1), shown below, from a viewpoint of usefulness as a production intermediate for a polymerizable liquid-crystal compound or the like.

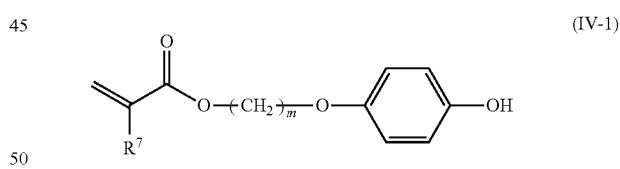

In formula (IV-1), $R^7$ is a hydrogen atom, a methyl group, or a chlorine atom.

Moreover, m is an integer of at least 1 and not more than 20, preferably an integer of at least 1 and not more than 12, and more preferably an integer of at least 2 and not more than 10.

Compounds of formula (IV-1) are commonly known substances that can be produced and acquired by conventional and commonly known methods (for example, refer to WO 2014/010325 A1).

Examples of bases that may be used in the present disclosure include organic bases such as triethylamine, diisopropylethylamine, phenyldimethylamine, pyridine, picoline, lutidine, and 4-(dimethylamino)pyridine; and inorganic bases such as sodium hydroxide, potassium hydroxide, magnesium hydroxide, calcium hydroxide, sodium carbonate, and potassium carbonate. One of these bases may be used individually, or two or more of these bases may be used in combination.

Of these bases, organic bases are preferable, tertiary amines such as triethylamine and diisopropylethylamine are more preferable, and triethylamine is particularly preferable from a viewpoint of obtaining the target with good yield.

The amount of base that is used per 1 mol of the acid halide compound (II) is normally at least 1 mol and not more than 3 mol, and preferably at least 1 mol and not more than 1.5 mol.

The esterification reaction may be carried out by, for example, adding the hydroxy compound (IV) into a water-immiscible organic solvent solution of the acid halide compound (II), adding the base to the resultant reaction mixture, and stirring the entire contents.

The reaction temperature is normally at least 0° C. and not higher than 80° C., preferably at least 0° C. and not higher than 50° C., and more preferably at least 0° C. and not higher than 30° C.

The reaction time is normally from a few minutes to several hours but is dependent on the scale of reaction and so forth.

The presently disclosed production method preferably includes a fifth step of, after the fourth step, washing the reaction liquid obtained through the fourth step with a weakly acidic buffer solution (normally a buffer solution having a pH of at least 4.5 and lower than 7), preferably with a buffer solution having a pH of at least 5.0 and not higher than 6.0, and more preferably with a buffer aqueous solution having a pH of at least 5.0 and not higher than 6.0.

In addition to the target monoester compound (V), the reaction liquid obtained through the fourth step normally contains a diester compound obtained as a by-product and residual dicarboxylic acid compound (I) present in the acid halide solution. In other words, a mixture that contains the target monoester compound (V) is obtained through the fourth step, and then the content of the dicarboxylic acid compound (I) and the like in this mixture can be reduced through inclusion of the fifth step. Consequently, it is possible to prevent the dicarboxylic acid compound (I) and the like from having a negative influence (reducing yield due to side reactions) during a reaction in a subsequent step.

The buffer solution is a solution that displays a buffering effect with respect to hydrogen ion concentration, and is normally obtained through mixing of a weak acid and its conjugate base or through mixing of a weak base and its conjugate acid. Through use of the buffer solution, it is possible to prevent hydrolysis of the target caused by a rapid change in pH, and thus it is possible to obtain the target with a good yield.

Examples of buffer solutions that may be used in the present disclosure include mixed buffer solutions such as a combination of acetic acid and sodium acetate, a combination of potassium hydrogen phthalate and sodium hydroxide, a combination of potassium dihydrogen phosphate and sodium hydroxide, a combination of sodium citrate and sodium hydroxide, and a combination of potassium dihydrogen phosphate and citric acid.

Of these buffer solutions, a mixed buffer solution of acetic acid and sodium acetate or a mixed buffer solution of potassium hydrogen phthalate and sodium hydroxide is preferable from a viewpoint of obtaining the effects of the present disclosure to a greater extent.

The buffer solution can be prepared by a conventional and commonly known method. For example, a mixed buffer solution of acetic acid and sodium acetate having a pH of 5.6 (18° C.) can be prepared by mixing 0.2 N acetic acid and 0.2 M sodium acetate aqueous solution in proportions of 1.9 mL of 0.2 N acetic acid and 18.1 mL of 0.2 M sodium acetate aqueous solution. Moreover, a mixed buffer solution of potassium hydrogen phthalate and sodium hydroxide having a pH of 5.8 (20° C.) can be prepared by mixing 0.2 M potassium hydrogen phthalate aqueous solution, 0.2 N sodium hydroxide aqueous solution, and water in proportions of 50.0 mL of potassium hydrogen phthalate aqueous solution, 43.0 mL of 0.2 N sodium hydroxide aqueous solution, and 107.0 mL of water.

The number of repetitions of washing of the reaction liquid with the buffer solution in the fifth step is not specifically limited, but is normally at least 1 and not more than 3. Washing with water may be performed after washing with the buffer solution.

The monoester compound (V) obtained as described above is useful, for example, as a production raw material for a polymerizable liquid-crystal compound of the following formula (5) (for example, refer to WO 2014/010325 A1).

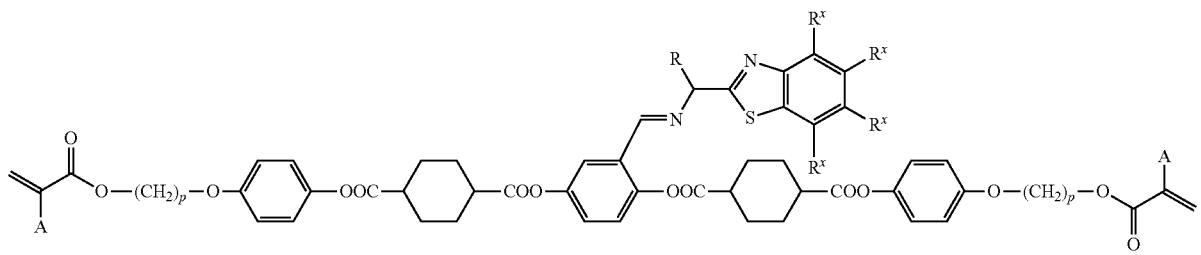

(In formula (5), A is a hydrogen atom, a methyl group, or a chlorine atom; R is a hydrogen atom or an organic group having a carbon number of at least 1 and not more than 20; each $R^X$ is independently a hydrogen atom, a halogen atom, an alkyl group having a carbon number of at least 1 and not more than 6, a cyano group, a nitro group, a fluoroalkyl group having a carbon number of at least 1 and not more than 6, an alkoxy group having a carbon number of at least 1 and not more than 6, or —C(=O)—O—$R^a$, where $R^a$ is a hydrogen atom or an optionally substituted alkyl group having a carbon number of at least 1 and not more than 10; and p is an integer of at least 1 and not more than 20.)

The polymerizable liquid-crystal compound of formula (5) can be produced, for example, by the following process.

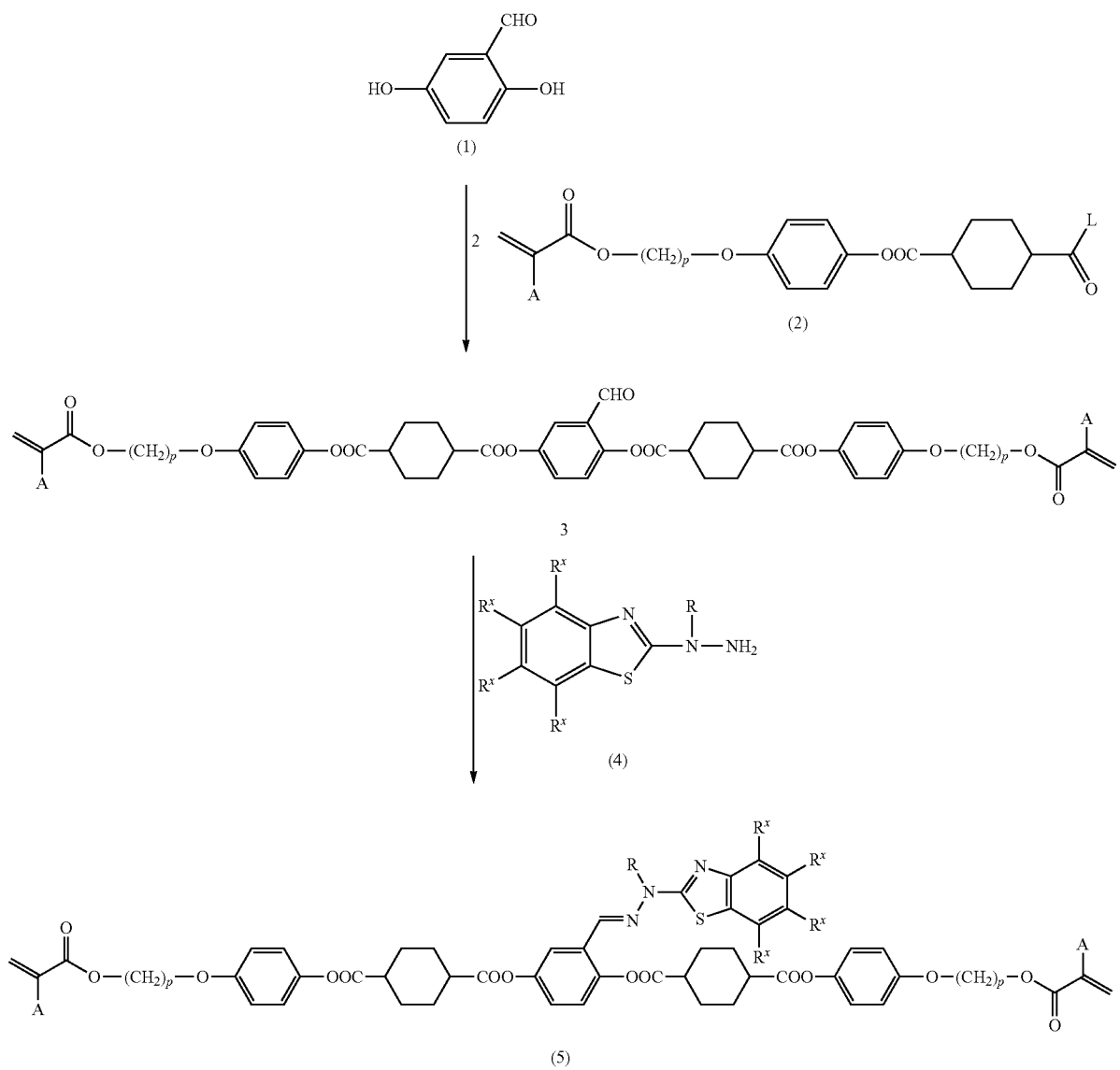

(In the preceding formula, A, R, $R^x$, and p are the same as previously explained; and L is a leaving group such as a hydroxy group, a halogen atom, an alkylsulfonyloxy group, or an arylsulfonyloxy group.)

In other words, the target polymerizable liquid-crystal compound of formula (5) can be obtained by reacting an aldehyde compound of formula (1) and a carboxylic acid monoester of formula (2) as the monoester compound (V) to obtain a compound of formula (3), and then reacting the compound of formula (3) and a hydrazine compound of formula (4).

In each of the reactions, the reaction temperature is normally at least 0° C. and not higher than 80° C., preferably at least 5° C. and not higher than 50° C., and more preferably at least 5° C. and not higher than 30° C.

The reaction time is normally from a few minutes to several hours but is dependent on the scale of reaction and so forth.

Examples

The following provides a more detailed description of the present disclosure through examples. However, the present disclosure is not in any way limited by the following examples.

(Example 1) Preparation of Solution of Dicarboxylic Acid Chloride Dissolved in Cyclopentyl Methyl Ether (CPME)

A three-necked reaction vessel equipped with a thermometer was charged with 10.0 g (58.08 mmol) of trans-1,4-cyclohexanedicarboxylic acid as a dicarboxylic acid compound (I), 100 g of cyclopentyl methyl ether (CPME) as a water-immiscible organic solvent, and 10.61 g (145 mmol) of N,N-dimethylformamide as an activator in a stream of nitrogen, and the reaction vessel was immersed in an ice bath to obtain a reaction liquid internal temperature of 0° C. Next, 17.63 g (145 mmol) of thionyl chloride as a halogenating agent was slowly dripped into the reaction vessel over 5 minutes while maintaining a reaction liquid internal temperature of 10° C. or lower. After completion of this dripping, the entire contents of the reaction vessel were further stirred for 1 hour at 25° C.

The contents of the reaction vessel were left at rest for 10 minutes after the end of the reaction and then a liquid separation operation was carried out to extract an oily liquid that was immiscible with the organic layer. Thereafter, the resultant organic layer was concentrated by a rotary evaporator to remove 80 mass % (80 g) of the used CPME and thereby prepare a solution of a dicarboxylic acid chloride (trans-1,4-cyclohexanedicarboxylic acid dichloride) dissolved in CPME. The prepared solution is referred to as acid chloride solution (A).

(Example 2) Preparation of Solution of Dicarboxylic Acid Chloride Dissolved in Toluene A solution of a dicarboxylic acid chloride (trans-1,4-cyclohexanedicarboxylic acid dichloride) dissolved in toluene was prepared by carrying out operations in the same manner as in Example 1 with the exception that, in Example 1, the water-immiscible organic solvent was changed from 100 g of CPME to 100 g of toluene. The prepared solution is referred to as acid chloride solution (B).

(Example 3) Preparation of Solution of Dicarboxylic Acid Chloride Dissolved in Mixed Solvent of Cyclohexane and Toluene A solution of a dicarboxylic acid chloride (trans-1,4-cyclohexanedicarboxylic acid dichloride) dissolved in a mixed solvent of cyclohexane and toluene was prepared by carrying out operations in the same manner as in Example 1 with the exception that, in Example 1, the water-immiscible organic solvent was changed from 100 g of CPME to a mixed solvent of 50 g of cyclohexane and 50 g of toluene. The prepared solution is referred to as acid chloride solution (C).

(Example 4) Preparation of Solution of Dicarboxylic Acid Chloride Dissolved in CPME A solution of a dicarboxylic acid chloride (trans-1,4-cyclohexanedicarboxylic acid dichloride) dissolved in CPME was prepared by carrying out operations in the same manner as in Example 1 with the exception that, in Example 1, 10.61 g (145 mmol) of N,N-dimethylformamide used as an activator was changed to 12.65 g (145 mmol) of N,N-dimethylacetamide. The prepared solution is referred to as acid chloride solution (D).

(Example 5) Preparation of Solution of Dicarboxylic Acid Chloride Dissolved in Toluene A solution of a dicarboxylic acid chloride (trans-1,4-cyclohexanedicarboxylic acid dichloride) dissolved in toluene was prepared by carrying out operations in the same manner as in Example 4 with the exception that, in Example 4, the water-immiscible organic solvent was changed from 100 g of CPME to 100 g of toluene. The prepared solution is referred to as acid chloride solution (E).

(Example 6) Preparation of Solution of Dicarboxylic Acid Chloride Dissolved in CPME A solution of a dicarboxylic acid chloride (trans-1,4-cyclohexanedicarboxylic acid dichloride) dissolved in CPME was prepared by carrying out operations in the same manner as in Example 1 with the exception that, in Example 1, 10.61 g (145 mmol) of N,N-dimethylformamide used as an activator was changed to 14.39 g (145 mmol) of N-methylpyrrolidone. The prepared solution is referred to as acid chloride solution (F).

(Example 7) Preparation of Solution of Dicarboxylic Acid Chloride Dissolved in Toluene A solution of a dicarboxylic acid chloride (trans-1,4-cyclohexanedicarboxylic acid dichloride) dissolved in toluene was prepared by carrying out operations in the same manner as in Example 6 with the exception that, in Example 6, the water-immiscible organic solvent was changed from 100 g of CPME to 100 g of toluene. The prepared solution is referred to as acid chloride solution (G).

(Example 8) Preparation of Solution of Dicarboxylic Acid Chloride Dissolved in CPME A solution of a dicarboxylic acid chloride (trans-1,4-cyclohexanedicarboxylic acid dichloride) dissolved in CPME was prepared by carrying out operations in the same manner as in Example 1 with the exception that, in Example 1, 10.61 g (145 mmol) of N,N-dimethylformamide used as an activator was changed to 16.57 g (145 mmol) of 1,3-dimethyl-2-imidazolidinone. The prepared solution is referred to as acid chloride solution (H).

(Example 9) Preparation of Solution of Dicarboxylic Acid Chloride Dissolved in Mixed Solvent of Cyclohexane and Toluene A solution of a dicarboxylic acid chloride (trans-1,4-cyclohexanedicarboxylic acid dichloride) dissolved in a mixed solvent of cyclohexane and toluene was prepared by carrying out operations in the same manner as in Example 8 with the exception that, in Example 8, the water-immiscible organic solvent was changed from 100 g of CPME to a mixed solvent of 50 g of cyclohexane and 50 g of toluene. The prepared solution is referred to as acid chloride solution (I).

(Example 10) Preparation of Solution of Dicarboxylic Acid Chloride Dissolved in CPME A three-necked reaction vessel equipped with a thermometer was charged with 10.0 g (58.08 mmol) of trans-1,4-cyclohexanedicarboxylic acid as a dicarboxylic acid compound (I) and 100 g of CPME as a water-immiscible organic solvent in a stream of nitrogen. The reaction vessel was further charged with 14.55 g (63.89 mmol) of benzyltriethylammonium chloride as an activator. Thereafter, 14.81 g (122 mmol) of thionyl chloride as a halogenating agent was slowly dripped into the reaction vessel over 5 minutes at 23° C. After completion of this dripping, the entire contents of the reaction vessel were heated to 40° C. and were further stirred for 30 minutes in this state.

The contents of the reaction vessel were left at rest for 10 minutes after the end of the reaction and then a liquid separation operation was carried out to extract an oily liquid that was immiscible with the organic layer. Thereafter, the resultant organic layer was concentrated by a rotary evaporator to remove 80 mass % (80 g) of the used CPME and thereby prepare a solution of a dicarboxylic acid chloride (trans-1,4-cyclohexanedicarboxylic acid dichloride) dissolved in CPME. The prepared solution is referred to as acid chloride solution (J).

(Example 11) Preparation of Solution of Dicarboxylic Acid Chloride Dissolved in Toluene A solution of a dicarboxylic acid chloride (trans-1,4-cyclohexanedicarboxylic acid dichloride) dissolved in toluene was prepared by carrying out operations in the same manner as in Example 10 with the exception that, in Example 10, the water-immiscible organic solvent was changed from 100 g of CPME to 100 g of toluene. The prepared solution is referred to as acid chloride solution (K).

(Example 12) Preparation of Solution of Dicarboxylic Acid Chloride Dissolved in CPME A solution of a dicarboxylic acid chloride (trans-1,4-cyclohexanedicarboxylic acid dichloride) dissolved in CPME was prepared by carrying out operations in the same manner as in Example 10 with the exception that, in Example 10, 14.55 g (63.89 mmol) of benzyltriethylammonium chloride used as an activator was changed to 25.82 g (63.89 mmol) of tri(n-octyl)methylammonium chloride (product name: Aliquat). The prepared solution is referred to as acid chloride solution (L).

(Example 13) Preparation of Solution of Dicarboxylic Acid Chloride Dissolved in Toluene A solution of a dicarboxylic acid chloride dissolved in toluene was prepared by carrying out operations in the same manner as in Example 12 with the exception that, in Example 12, the water-immiscible organic solvent was changed from 100 g of CPME to 100 g of toluene. The prepared solution is referred to as acid chloride solution (M).

(Example 14) Preparation of Solution of Dicarboxylic Acid Chloride Dissolved in Toluene A solution of a dicarboxylic acid chloride (trans-1,4-cyclohexanedicarboxylic acid dichloride) dissolved in toluene was prepared by carrying out operations in the same manner as in Example 13 with the exception that, in Example 13, 25.82 g (63.89 mmol) of tri(n-octyl)methylammonium chloride (product name: Aliquat) used as an activator was changed to 25.82 g (63.89 mmol) of a methyltrioctylammonium chloride mixture (product name: Adogen). The prepared solution is referred to as acid chloride solution (N).

(Example 15) Production of Mixture 1

A three-necked reaction vessel equipped with a thermometer was charged with the acid chloride solution (A) prepared in Example 1 and subsequently with 222 g of CPME in a stream of nitrogen. The reaction vessel was immersed in an ice bath to obtain a reaction liquid internal temperature of 0° C. The reaction vessel was then charged with 14.58 g (55.17 mmol) of 4-(6-acryloyloxy-hex-1-yloxy)phenol (produced by DKSH) as a hydroxy compound (IV). Next, 6.70 g (66.21 mmol) of triethylamine as a base was slowly dripped into the reaction vessel over 5 minutes while maintaining a reaction liquid internal temperature of 10° C. or lower. After completion of this dripping, the entire contents of the reaction vessel were further stirred for 1 hour at 0° C.

The resultant reaction liquid was washed for 2 hours at 25° C. with addition of 36 g of distilled water, and then the water layer was extracted. The organic layer was washed three times with 61 g of a buffer solution (pH: 5.5) composed of an aqueous solution of a mixture of acetic acid and sodium acetate with a concentration of 1 mol/L, and then the buffer solution was extracted.

Washing was subsequently performed once with 36 g of distilled water. Crystals were precipitated from the resultant organic layer through addition of 365 mL of n-hexane and the precipitated crystals were collected by filtration. The obtained crystals were washed with 18 mL of n-hexane and were subsequently vacuum dried to yield 17.67 g of a mixture 1 in the form of a white solid. The obtained crystals were analyzed by high-performance liquid chromatography (HPLC), and quantification of monoester and diester was performed using a calibration curve. It was confirmed that the crystals contained 12.10 g (28.91 mmol) of a target monoester and 5.58 g (8.39 mmol) of a diester.

(Example 16) Production of Mixture 2

Operations were carried out in the same manner as in Example 15 with the exception that, in Example 15, the acid chloride solution (B) prepared in Example 2 was used instead of the acid chloride solution (A) prepared in Example 1. As a result, 17.35 g of a white solid was obtained. It was confirmed that the solid contained 11.54 g (27.57 mmol) of a target monoester and 5.81 g (8.74 mmol) of a diester by determining the composition of the solid through the same method as in Example 15.

(Example 17) Production of Mixture 3

Operations were carried out in the same manner as in Example 15 with the exception that, in Example 15, the acid chloride solution (C) prepared in Example 3 was used instead of the acid chloride solution (A) prepared in

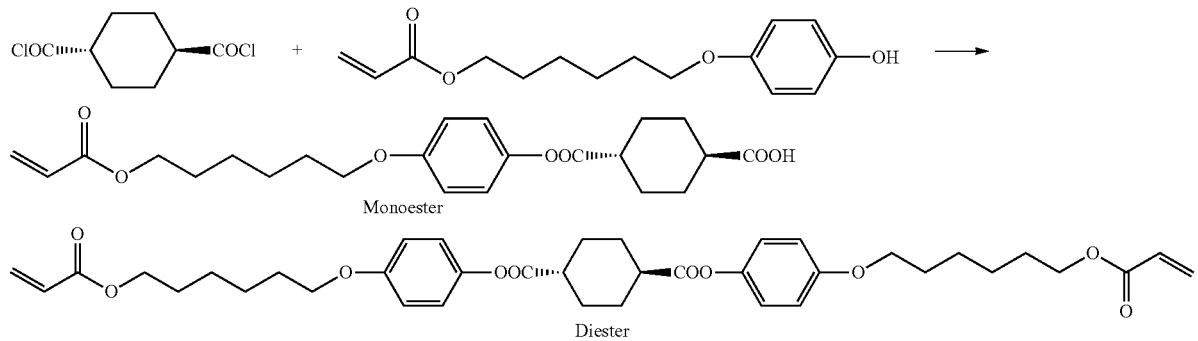

Example 1. As a result, 17.43 g of a white solid was obtained. It was confirmed that the solid contained 11.55 g (27.61 mmol) of a target monoester and 5.88 g (8.84 mmol) of a diester by determining the composition of the solid through the same method as in Example 15.

(Example 18) Production of Mixture 4

Operations were carried out in the same manner as in Example 15 with the exception that, in Example 15, the acid chloride solution (D) prepared in Example 4 was used instead of the acid chloride solution (A) prepared in Example 1. As a result, 17.52 g of a white solid was obtained. It was confirmed that the solid contained 11.98 g (28.62 mmol) of a target monoester and 5.54 g (8.33 mmol) of a diester by determining the composition of the solid through the same method as in Example 15.

(Example 19) Production of Mixture 5

Operations were carried out in the same manner as in Example 15 with the exception that, in Example 15, the acid chloride solution (E) prepared in Example 5 was used instead of the acid chloride solution (A) prepared in Example 1. As a result, 17.51 g of a white solid was obtained. It was confirmed that the solid contained 11.57 g (27.65 mmol) of a target monoester and 5.94 g (8.93 mmol) of a diester by determining the composition of the solid through the same method as in Example 15.

(Example 20) Production of Mixture 6

Operations were carried out in the same manner as in Example 15 with the exception that, in Example 15, the acid chloride solution (F) prepared in Example 6 was used instead of the acid chloride solution (A) prepared in Example 1. As a result, 17.47 g of a white solid was obtained. It was confirmed that the solid contained 12.04 g (28.76 mmol) of a target monoester and 5.43 g (8.17 mmol) of a diester by determining the composition of the solid through the same method as in Example 15.

(Example 21) Production of Mixture 7

Operations were carried out in the same manner as in Example 15 with the exception that, in Example 15, the acid chloride solution (G) prepared in Example 7 was used instead of the acid chloride solution (A) prepared in Example 1. As a result, 17.54 g of a white solid was obtained. It was confirmed that the solid contained 11.59 g (27.70 mmol) of a target monoester and 5.94 g (8.94 mmol) of a diester by determining the composition of the solid through the same method as in Example 15.

(Example 22) Production of Mixture 8

Operations were carried out in the same manner as in Example 15 with the exception that, in Example 15, the acid chloride solution (H) prepared in Example 8 was used instead of the acid chloride solution (A) prepared in Example 1. As a result, 17.56 g of a white solid was obtained. It was confirmed that the solid contained 12.02 g (28.73 mmol) of a target monoester and 5.54 g (8.33 mmol) of a diester by determining the composition of the solid through the same method as in Example 15.

(Example 23) Production of Mixture 9

Operations were carried out in the same manner as in Example 15 with the exception that, in Example 15, the acid chloride solution (I) prepared in Example 9 was used instead of the acid chloride solution (A) prepared in Example 1. As a result, 17.46 g of a white solid was obtained. It was confirmed that the solid contained 11.57 g (27.65 mmol) of a target monoester and 5.89 g (8.86 mmol) of a diester by determining the composition of the solid through the same method as in Example 15.

(Example 24) Production of Mixture 10

Operations were carried out in the same manner as in Example 15 with the exception that, in Example 15, the acid chloride solution (J) prepared in Example 10 was used instead of the acid chloride solution (A) prepared in Example 1. As a result, 18.11 g of a white solid was obtained. It was confirmed that the solid contained 11.96 g (28.57 mmol) of a target monoester and 6.16 g (9.26 mmol) of a diester by determining the composition of the solid through the same method as in Example 15.

(Example 25) Production of Mixture 11

Operations were carried out in the same manner as in Example 15 with the exception that, in Example 15, the acid chloride solution (K) prepared in Example 11 was used instead of the acid chloride solution (A) prepared in Example 1. As a result, 18.01 g of a white solid was obtained. It was confirmed that the solid contained 11.87 g (28.35 mmol) of a target monoester and 6.14 g (9.24 mmol) of a diester by determining the composition of the solid through the same method as in Example 15.

(Example 26) Production of Mixture 12

Operations were carried out in the same manner as in Example 15 with the exception that, in Example 15, the acid chloride solution (L) prepared in Example 12 was used instead of the acid chloride solution (A) prepared in Example 1. As a result, 17.93 g of a white solid was obtained. It was confirmed that the solid contained 11.89 g (28.41 mmol) of a target monoester and 6.05 g (9.09 mmol) of a diester by determining the composition of the solid through the same method as in Example 15.

(Example 27) Production of Mixture 13

Operations were carried out in the same manner as in Example 15 with the exception that, in Example 15, the acid chloride solution (M) prepared in Example 13 was used instead of the acid chloride solution (A) prepared in Example 1. As a result, 17.98 g of a white solid was obtained. It was confirmed that the solid contained 11.79 g (28.17 mmol) of a target monoester and 6.19 g (9.31 mmol) of a diester by determining the composition of the solid through the same method as in Example 15.

(Example 28) Production of Mixture 14

Operations were carried out in the same manner as in Example 15 with the exception that, in Example 15, the acid chloride solution (N) prepared in Example 14 was used instead of the acid chloride solution (A) prepared in Example 1. As a result, 17.96 g of a white solid was obtained. It was confirmed that the solid contained 11.89 g (28.42 mmol) of a target monoester and 6.07 g (9.13 mmol)

of a diester by determining the composition of the solid through the same method as in Example 15.

(Comparative Example 1) Preparation of Solution of Dicarboxylic Acid Chloride and N,N-Dimethylformamide Dissolved in CPME A three-necked reaction vessel equipped with a thermometer was charged with 10.0 g (58.08 mmol) of trans-1,4-cyclohexanedicarboxylic acid as a dicarboxylic acid compound (I), 100 g of CPME as a water-immiscible organic solvent, and 425 mg (5.81 mmol) of N,N-dimethylformamide as an activator in a stream of nitrogen. Thereafter, 14.81 g (122 mmol) of thionyl chloride as a halogenating agent was slowly dripped into the reaction vessel over 5 minutes at 23° C. After completion of this dripping, the entire contents of the reaction vessel were heated to 50° C. and further stirred for 5 hours.

After the end of the reaction, concentrating was carried out by a rotary evaporator in a state in which an oily liquid that was immiscible with the organic layer was present, without performing a liquid separation operation, to extract 80 mass % (80 g) of the used CPME and thereby prepare a solution of a dicarboxylic acid chloride (trans-1,4-cyclohexanedicarboxylic acid dichloride) and N,N-dimethylformamide dissolved in CPME. The prepared solution is referred to as acid chloride solution (a).

(Comparative Example 2) Preparation of Solution of Dicarboxylic Acid Chloride and N,N-Dimethylacetamide Dissolved in CPME A solution of a dicarboxylic acid chloride (trans-1,4-cyclohexanedicarboxylic acid dichloride) and N,N-dimethylacetamide dissolved in CPME was prepared by carrying out operations in the same manner as in Comparative Example 1 with the exception that, in Comparative Example 1, 425 mg (5.81 mmol) of N,N-dimethylformamide used as an activator was changed to 506 mg (5.81 mmol) of N,N-dimethylacetamide. The prepared solution is referred to as acid chloride solution (b).

(Comparative Example 3) Preparation of Solution of Dicarboxylic Acid Chloride and N,N-Dimethylformamide Dissolved in CPME A three-necked reaction vessel equipped with a thermometer was charged with 10.0 g (58.08 mmol) of trans-1,4-cyclohexanedicarboxylic acid as a dicarboxylic acid compound (I), 100 g of CPME as a water-immiscible organic solvent, and 10.61 g (145 mmol) of N,N-dimethylformamide as an activator in a stream of nitrogen, and the reaction vessel was immersed in an ice bath to obtain a reaction liquid internal temperature of 0° C. Next, 17.63 g (145 mmol) of thionyl chloride as a halogenating agent was slowly dripped into the reaction vessel over 5 minutes while maintaining a reaction liquid internal temperature of 10° C. or lower. After completion of this dripping, the entire contents of the reaction vessel were further stirred for 1 hour at 25° C.

After the end of the reaction, concentrating was carried out by a rotary evaporator in a state in which an oily liquid that was immiscible with the organic layer was present, without performing a liquid separation operation, to extract 80 mass % (80 g) of the used CPME and thereby prepare a solution of a dicarboxylic acid chloride (trans-1,4-cyclohexanedicarboxylic acid dichloride) and N,N-dimethylformamide dissolved in CPME. The prepared solution is referred to as acid chloride solution (c).

(Comparative Example 4) Preparation of Solution of Dicarboxylic Acid Chloride and N,N-Dimethylacetamide Dissolved in Toluene A solution of a dicarboxylic acid chloride (trans-1,4-cyclohexanedicarboxylic acid dichloride) and N,N-dimethylacetamide dissolved in toluene was prepared by carrying out operations in the same manner as in Comparative Example 3 with the exception that, in Comparative Example 3, 10.61 g (145 mmol) of N,N-dimethylformamide used as an activator was changed to 12.65 g (145 mmol) of N,N-dimethylacetamide, and the water-immiscible organic solvent was changed from 100 g of CPME to 100 g of toluene. The prepared solution is referred to as acid chloride solution (d).

(Comparative Example 5) Preparation of Solution of Dicarboxylic Acid Chloride and N-Methylpyrrolidone (NMP) Dissolved in CPME A solution of a dicarboxylic acid chloride (trans-1,4-cyclohexanedicarboxylic acid dichloride) and N-methylpyrrolidone dissolved in CPME was prepared by carrying out operations in the same manner as in Comparative Example 3 with the exception that, in Comparative Example 3, 10.61 g (145 mmol) of N,N-dimethylformamide used as an activator was changed to 14.39 g (145 mmol) of N-methylpyrrolidone. The prepared solution is referred to as acid chloride solution (e).

(Comparative Example 6) Preparation of Solution of Dicarboxylic Acid Chloride and 1,3-Dimethyl-2-Imidazolidinone Dissolved in Mixed Solvent of Cyclohexane and Toluene A solution of a dicarboxylic acid chloride (trans-1,4-cyclohexanedicarboxylic acid dichloride) and 1,3-dimethyl-2-imidazolidinone dissolved in a mixed solvent of cyclohexane and toluene was prepared by carrying out operations in the same manner as in Comparative Example 3 with the exception that, in Comparative Example 3, 10.61 g (145 mmol) of N,N-dimethylformamide used as an activator was changed to 16.57 g (145 mmol) of 1,3-dimethyl-2-imidazolidinone, and the water-immiscible organic solvent was changed from 100 g of cyclopentyl methyl ether (CPME) to a mixed solvent of 50 g of cyclohexane and 50 g of toluene. The prepared solution is referred to as acid chloride solution (f).

(Comparative Example 7) Preparation of Solution of Dicarboxylic Acid Chloride and N,N-Dimethylformamide (DMF) Dissolved in Cyclopentyl Methyl Ether (CPME)

A solution of a dicarboxylic acid chloride (trans-1,4-cyclohexanedicarboxylic acid dichloride) and N,N-dimethylformamide dissolved in CPME was prepared by carrying out operations in the same manner as in Comparative Example 3. The prepared solution is referred to as acid chloride solution (g).

(Comparative Example 8) Preparation of Solution of Dicarboxylic Acid Chloride and N,N-Dimethylformamide (DMF) Dissolved in Cyclopentyl Methyl Ether (CPME)

A solution of a dicarboxylic acid chloride (trans-1,4-cyclohexanedicarboxylic acid dichloride) and N,N-dimethylformamide dissolved in CPME was prepared by carrying out operations in the same manner as in Comparative Example 3. The prepared solution is referred to as acid chloride solution (h).

(Comparative Example 9) Preparation of Solution of Dicarboxylic Acid Chloride and Benzyltriethylammonium Chloride Dissolved in CPME A three-necked reaction vessel equipped with a thermometer was charged with 10.0 g (58.08 mmol) of trans-1,4-cyclohexanedicarboxylic acid as a dicarboxylic acid compound (I) and 100 g of CPME as a water-immiscible organic solvent in a stream of nitrogen. The reaction vessel was further charged with 14.55 g (63.89 mmol) of benzyltriethylammonium chloride as an activator. Thereafter, 14.81 g (122 mmol) of thionyl chloride as a halogenating agent was slowly dripped into the reaction vessel over 5 minutes at 23° C. After completion of this dripping, the entire contents of the reaction vessel were heated to 40° C. and further stirred for 30 minutes in this state.

After the end of the reaction, concentrating was carried out by a rotary evaporator in a state in which an oily liquid that was immiscible with the organic layer was present, without performing a liquid separation operation, to extract 80 mass % (80 g) of the used CPME and thereby prepare a solution of a dicarboxylic acid chloride (trans-1,4-cyclohexanedicarboxylic acid dichloride) and benzyltriethylammonium chloride dissolved in CPME. The prepared solution is referred to as acid chloride solution (i).

(Comparative Example 10) Preparation of Solution of Dicarboxylic Acid Chloride and Tri(n-Octyl)Methylammonium Chloride Dissolved in Toluene A solution of a dicarboxylic acid chloride (trans-1,4-cyclohexanedicarboxylic acid dichloride) and tri(n-octyl)methylammonium chloride dissolved in toluene was prepared by carrying out operations in the same manner as in Comparative Example 9 with the exception that, in Comparative Example 9, 14.55 g (63.89 mmol) of benzyltriethylammonium chloride used as an activator was changed to 25.82 g (63.89 mmol) of tri(n-octyl)methylammonium chloride (product name: Aliquat), and the water-immiscible organic solvent was changed from 100 g of CPME to 100 g of toluene. The prepared solution is referred to as acid chloride solution (j).

(Comparative Example 11) Preparation of Solution of Dicarboxylic Acid Chloride and Methyltrioctylammonium Chloride Mixture Dissolved in CPME A solution of a dicarboxylic acid chloride (trans-1,4-cyclohexanedicarboxylic acid dichloride) and a methyltrioctylammonium chloride mixture dissolved in CPME was prepared by carrying out operations in the same manner as in Comparative Example 9 with the exception that, in Comparative Example 9, 14.55 g (63.89 mmol) of benzyltriethylammonium chloride used as an activator was changed to 25.82 g (63.89 mmol) of a methyltrioctylammonium chloride mixture (product name: Adogen). The prepared solution is referred to as acid chloride solution (k).

(Comparative Example 12) Preparation of Solution of Dicarboxylic Acid Chloride and Benzyltriethylammonium Chloride Dissolved in CPME A solution of a dicarboxylic acid chloride (trans-1,4-cyclohexanedicarboxylic acid dichloride) and benzyltriethylammonium chloride dissolved in CPME was prepared by carrying out operations in the same manner as in Comparative Example 9. The prepared solution is referred to as acid chloride solution (1).

(Comparative Example 13) Preparation of Solution of Dicarboxylic Acid Chloride and Methyltrioctylammonium Chloride Mixture Dissolved in CPME A solution of a dicarboxylic acid chloride (trans-1,4-cyclohexanedicarboxylic acid dichloride) and a methyltrioctylammonium chloride mixture dissolved in CPME was prepared by carrying out operations in the same manner as in Comparative Example 11. The prepared solution is referred to as acid chloride solution (m).

(Comparative Example 14) Synthesis of Mixture 15

A three-necked reaction vessel equipped with a thermometer was charged with the acid chloride solution (a) prepared in Comparative Example 1 and subsequently with 222 g of CPME in a stream of nitrogen, and the reaction vessel was immersed in an ice bath to obtain a reaction liquid internal temperature of 0° C. The reaction vessel was then charged with 14.58 g (55.17 mmol) of 4-(6-acryloyloxy-hex-1-yloxy)phenol (produced by DKSH) as a hydroxy compound (IV). Next, 6.70 g (66.21 mmol) of triethylamine as a base was slowly dripped into the reaction vessel over 5 minutes while maintaining a reaction liquid internal temperature of 10° C. or lower. After completion of this dripping, the entire contents of the reaction vessel were further stirred for 1 hour at 0° C.

The resultant reaction liquid was washed for 2 hours at 25° C. with addition of 36 g of distilled water, and then the water layer was extracted. The organic layer was washed three times with 61 g of a buffer solution (pH: 5.5) composed of an aqueous solution of a mixture of acetic acid and sodium acetate with a concentration of 1 mol/L, and then the buffer solution was extracted.

Washing was subsequently performed once with 36 g of distilled water. Crystals were precipitated from the resultant organic layer through addition of 365 mL of n-hexane and the precipitated crystals were collected by filtration. The obtained crystals were washed with 18 mL of n-hexane and were subsequently vacuum dried to yield 15.56 g of a mixture 15 in the form of a white solid. The obtained crystals were analyzed by high-performance liquid chromatography (HPLC), and quantification of monoester and diester was performed using a calibration curve. It was confirmed that the crystals contained 9.93 g (23.73 mmol) of a target monoester and 5.63 g (8.47 mmol) of a diester.

(Comparative Example 15) Synthesis of Mixture 16

Operations were carried out in the same manner as in Comparative Example 14 with the exception that, in Comparative Example 14, the acid chloride solution (b) prepared in Comparative Example 2 was used instead of the acid chloride solution (a) prepared in Comparative Example 1.

As a result, 15.72 g of a white solid was obtained. It was confirmed that the solid contained 10.06 g (24.03 mmol) of a target monoester and 5.67 g (8.52 mmol) of a diester by determining the composition of the solid through the same method as in Comparative Example 14.

(Comparative Example 16) Synthesis of Mixture 17

Operations were carried out in the same manner as in Comparative Example 14 with the exception that, in Comparative Example 14, the acid chloride solution (c) prepared in Comparative Example 3 was used instead of the acid chloride solution (a) prepared in Comparative Example 1. As a result, 2.79 g of a white solid was obtained. It was confirmed that the solid contained 2.45 g (5.84 mmol) of a target monoester and 0.34 g (0.52 mmol) of a diester by determining the composition of the solid through the same method as in Comparative Example 14.

(Comparative Example 17) Synthesis of Mixture 18

Operations were carried out in the same manner as in Comparative Example 14 with the exception that, in Comparative Example 14, the acid chloride solution (d) prepared in Comparative Example 4 was used instead of the acid chloride solution (a) prepared in Comparative Example 1. As a result, 2.66 g of a white solid was obtained. It was confirmed that the solid contained 2.29 g (5.47 mmol) of a target monoester and 0.37 g (0.56 mmol) of a diester by determining the composition of the solid through the same method as in Comparative Example 14.

(Comparative Example 18) Synthesis of Mixture 19

Operations were carried out in the same manner as in Comparative Example 14 with the exception that, in Comparative Example 14, the acid chloride solution (e) prepared in Comparative Example 5 was used instead of the acid chloride solution (a) prepared in Comparative Example 1. As a result, 2.88 g of a white solid was obtained. It was confirmed that the solid contained 2.51 g (5.99 mmol) of a target monoester and 0.37 g (0.56 mmol) of a diester by determining the composition of the solid through the same method as in Comparative Example 14.

(Comparative Example 19) Synthesis of Mixture 20

Operations were carried out in the same manner as in Comparative Example 14 with the exception that, in Comparative Example 14, the acid chloride solution (f) prepared in Comparative Example 6 was used instead of the acid chloride solution (a) prepared in Comparative Example 1. As a result, 2.63 g of a white solid was obtained. It was confirmed that the solid contained 2.27 g (5.43 mmol) of a target monoester and 0.36 g (0.54 mmol) of a diester by determining the composition of the solid through the same method as in Comparative Example 14.

(Comparative Example 20) Synthesis of Mixture 21

Operations were carried out in the same manner as in Comparative Example 14 with the exception that, in Comparative Example 14, the acid chloride solution (g) prepared in Comparative Example 7 was used instead of the acid chloride solution (a) prepared in Comparative Example 1, and the amount of triethylamine was changed from 6.70 g (66.21 mmol) to 14.0 g (138 mmol). As a result, 4.74 g of a white solid was obtained. It was confirmed that the solid contained 3.44 g (8.22 mmol) of a target monoester and 1.31 g (1.96 mmol) of a diester by determining the composition of the solid through the same method as in Comparative Example 14.

(Comparative Example 21) Synthesis of Mixture 22

Operations were carried out in the same manner as in Comparative Example 14 with the exception that, in Comparative Example 14, the acid chloride solution (h) prepared in Comparative Example 8 was used instead of the acid chloride solution (a) prepared in Comparative Example 1, and the amount of triethylamine was changed from 6.70 g (66.21 mmol) to 27.9 g (276 mmol). As a result, 10.67 g of a white solid was obtained. It was confirmed that the solid contained 5.80 g (13.85 mmol) of a target monoester and 4.87 g (7.32 mmol) of a diester by determining the composition of the solid through the same method as in Comparative Example 14.

(Comparative Example 22) Synthesis of Mixture 23

Operations were carried out in the same manner as in Comparative Example 14 with the exception that, in Comparative Example 14, the acid chloride solution (i) prepared in Comparative Example 9 was used instead of the acid chloride solution (a) prepared in Comparative Example 1. As a result, 15.03 g of a white solid was obtained. It was confirmed that the solid contained 10.31 g (24.64 mmol) of a target monoester and 4.72 g (7.10 mmol) of a diester by determining the composition of the solid through the same method as in Comparative Example 14.

(Comparative Example 23) Synthesis of Mixture 24

Operations were carried out in the same manner as in Comparative Example 14 with the exception that, in Comparative Example 14, the acid chloride solution (j) prepared in Comparative Example 10 was used instead of the acid chloride solution (a) prepared in Comparative Example 1. As a result, 15.11 g of a white solid was obtained. It was confirmed that the solid contained 10.36 g (24.77 mmol) of a target monoester and 4.75 g (7.14 mmol) of a diester by determining the composition of the solid through the same method as in Comparative Example 14.

(Comparative Example 24) Synthesis of Mixture 25

Operations were carried out in the same manner as in Comparative Example 14 with the exception that, in Comparative Example 14, the acid chloride solution (k) prepared in Comparative Example 11 was used instead of the acid chloride solution (a) prepared in Comparative Example 1. As a result, 14.87 g of a white solid was obtained. It was confirmed that the solid contained 10.21 g (24.39 mmol) of a target monoester and 4.67 g (7.02 mmol) of a diester by determining the composition of the solid through the same method as in Comparative Example 14.

(Comparative Example 25) Synthesis of Mixture 26

Operations were carried out in the same manner as in Comparative Example 14 with the exception that, in Comparative Example 14, the acid chloride solution (1) prepared in Comparative Example 12 was used instead of the acid chloride solution (a) prepared in Comparative Example 1, and the amount of triethylamine was changed from 6.70 g (66.21 mmol) to 8.93 g (88.28 mmol). As a result, 16.12 g of a white solid was obtained. It was confirmed that the solid contained 10.39 g (24.82 mmol) of a target monoester and 5.73 g (8.62 mmol) of a diester by determining the composition of the solid through the same method as in Comparative Example 14.

(Comparative Example 26) Synthesis of Mixture 27

Operations were carried out in the same manner as in Comparative Example 14 with the exception that, in Comparative Example 14, the acid chloride solution (m) prepared in Comparative Example 13 was used instead of the acid chloride solution (a) prepared in Comparative Example 1, and the amount of triethylamine was changed from 6.70 g (66.21 mmol) to 8.93 g (88.28 mmol). As a result, 16.33 g of a white solid was obtained. It was confirmed that the solid contained 10.56 g (25.23 mmol) of a target monoester and 5.77 g (8.69 mmol) of a diester by determining the composition of the solid through the same method as in Comparative Example 14.

The results described above are summarized in Tables 1 and 2.

In Tables 1 and 2, (T) to (Z) represent the following.
(T): N,N-Dimethylformamide
(U): N,N-Dimethylacetamide
(V): N-Methylpyrrolidone
(W): 1,3-Dimethyl-2-imidazolidinone
(X): Benzyltriethylammonium chloride
(Y): Tri(n-octyl)methylammonium chloride (product name: Aliquat)
(Z): Methyltrioctylammonium chloride mixture (product name: Adogen)

TABLE 1

| | | Acid chlorination reaction | | | | | | |
|---|---|---|---|---|---|---|---|---|
| | | Activator | | Water-immiscible organic solvent | Acid chloride solution | Temperature (° C.) | Time (h) | Conversion rate (%) | Liquid separation operation |
| | Type | Used amount*[1] (equivalents) | | | | | | |
| Example 1 | (T) | 2.5 | CPME | A | 25 | 1 | 99.2 | Yes |
| Example 2 | (T) | 2.5 | Toluene | B | 25 | 1 | 99.1 | Yes |
| Example 3 | (T) | 2.5 | Cyclohexane + Toluene*[2] | C | 25 | 1 | 99.5 | Yes |
| Example 4 | (U) | 2.5 | CPME | D | 25 | 1 | 99.6 | Yes |
| Example 5 | (U) | 2.5 | Toluene | E | 25 | 1 | 99.5 | Yes |
| Example 6 | (V) | 2.5 | CPME | F | 25 | 1 | 99.1 | Yes |
| Example 7 | (V) | 2.5 | Toluene | G | 25 | 1 | 99.4 | Yes |
| Example 8 | (W) | 2.5 | CPME | H | 25 | 1 | 99.5 | Yes |
| Example 9 | (W) | 2.5 | Cyclohexane + Toluene*[2] | I | 25 | 1 | 99.3 | Yes |
| Example 10 | (X) | 1.1 | CPME | J | 40 | 0.5 | 99.2 | Yes |
| Example 11 | (X) | 1.1 | Toluene | K | 40 | 0.5 | 99.7 | Yes |
| Example 12 | (Y) | 1.1 | CPME | L | 40 | 0.5 | 99.5 | Yes |
| Example 13 | (Y) | 1.1 | Toluene | M | 40 | 0.5 | 99.4 | Yes |
| Example 14 | (Z) | 1.1 | Toluene | N | 40 | 0.5 | 99.3 | Yes |
| Comparative Example 1 | (T) | 0.1 | CPME | a | 50 | 5 | 97.9 | No |
| Comparative Example 2 | (U) | 0.1 | CPME | b | 50 | 5 | 98.1 | No |
| Comparative Example 3 | (T) | 2.5 | CPME | c | 25 | 1 | 99.3 | No |
| Comparative Example 4 | (U) | 2.5 | Toluene | d | 25 | 1 | 99.4 | No |
| Comparative Example 5 | (V) | 2.5 | CPME | e | 25 | 1 | 99.5 | No |
| Comparative Example 6 | (W) | 2.5 | Cyclohexane + Toluene*[2] | f | 25 | 1 | 99.2 | No |
| Comparative Example 7 | (T) | 2.5 | CPME | g | 25 | 1 | 99.3 | No |
| Comparative Example 8 | (T) | 2.5 | CPME | h | 25 | 1 | 99.3 | No |
| Comparative Example 9 | (X) | 1.1 | CPME | i | 40 | 0.5 | 99.2 | No |
| Comparative Example 10 | (Y) | 1.1 | Toluene | j | 40 | 0.5 | 99.4 | No |
| Comparative Example 11 | (Z) | 1.1 | CPME | k | 40 | 0.5 | 99.3 | No |
| Comparative Example 12 | (X) | 1.1 | CPME | l | 40 | 0.5 | 99.2 | No |
| Comparative Example 13 | (Z) | 1.1 | CPME | m | 40 | 0.5 | 99.2 | No |

*[1]Based on used amount of trans-1,4-cyclohexanedicarboxylic acid
*[2]Cyclohexane/toluene = 1/1 (w/w) mixed solvent used

TABLE 2

| | Used acid chloride solution | Used amount of base*[3] (equivalents) | Obtained amount of mixture (g) | | | Reaction conversion rate (%) | Monoester content*[4] (wt %) |
|---|---|---|---|---|---|---|---|
| | | | Monoester | Diester | Total | | |
| Example 15 | A | 1.1 | 12.10 | 5.58 | 17.67 | 99.26 | 68.45 |
| Example 16 | B | 1.1 | 11.54 | 5.81 | 17.35 | 99.15 | 66.50 |
| Example 17 | C | 1.1 | 11.55 | 5.88 | 17.43 | 99.35 | 66.29 |
| Example 18 | D | 1.1 | 11.98 | 5.54 | 17.52 | 99.29 | 68.38 |
| Example 19 | E | 1.1 | 11.57 | 5.94 | 17.51 | 99.36 | 66.09 |
| Example 20 | F | 1.1 | 12.04 | 5.43 | 17.47 | 99.22 | 68.91 |
| Example 21 | G | 1.1 | 11.59 | 5.94 | 17.54 | 99.37 | 66.10 |
| Example 22 | H | 1.1 | 12.02 | 5.54 | 17.56 | 99.28 | 68.47 |
| Example 23 | I | 1.1 | 11.57 | 5.89 | 17.46 | 99.32 | 66.27 |
| Example 24 | J | 1.1 | 11.96 | 6.16 | 18.11 | 99.34 | 66.01 |
| Example 25 | K | 1.1 | 11.87 | 6.14 | 18.01 | 99.11 | 65.89 |
| Example 26 | L | 1.1 | 11.89 | 6.05 | 17.93 | 99.09 | 66.29 |
| Example 27 | M | 1.1 | 11.79 | 6.19 | 17.98 | 99.08 | 65.58 |
| Example 28 | N | 1.1 | 11.89 | 6.07 | 17.96 | 99.28 | 66.21 |
| Comparative Example 14 | a | 1.1 | 9.93 | 5.63 | 15.56 | 90.99 | 63.82 |
| Comparative Example 15 | b | 1.1 | 10.06 | 5.67 | 15.72 | 91.05 | 63.96 |
| Comparative Example 16 | c | 1.1 | 2.45 | 0.34 | 2.79 | 46.59 | 87.66 |
| Comparative Example 17 | d | 1.1 | 2.29 | 0.37 | 2.66 | 46.97 | 85.94 |
| Comparative Example 18 | e | 1.1 | 2.51 | 0.37 | 2.88 | 47.02 | 87.13 |
| Comparative Example 19 | f | 1.1 | 2.27 | 0.36 | 2.63 | 46.87 | 86.34 |
| Comparative Example 20 | g | 2.4 | 3.44 | 1.31 | 4.74 | 68.79 | 72.48 |
| Comparative Example 21 | h | 4.8 | 5.80 | 4.87 | 10.67 | 92.98 | 54.36 |
| Comparative Example 22 | i | 1.1 | 10.31 | 4.72 | 15.03 | 89.98 | 68.60 |
| Comparative Example 23 | j | 1.1 | 10.36 | 4.75 | 15.11 | 90.42 | 68.59 |
| Comparative Example 24 | k | 1.1 | 10.21 | 4.67 | 14.87 | 89.40 | 68.62 |
| Comparative Example 25 | l | 1.5 | 10.39 | 5.73 | 16.12 | 96.06 | 64.45 |
| Comparative Example 26 | m | 1.5 | 10.56 | 5.77 | 16.33 | 95.78 | 64.64 |

*[3]Based on used amount of 4-(6-acryloyloxy-hex-1-yloxy)phenol
*[4]Calculated from HPLC calibration curve It can be seen from Table 1 that by carrying out an acid chlorination reaction using at least 1.1 equivalents and not more than 3.0 equivalents of a nitrogen atom-containing polar aprotic solvent or a tetraalkylammonium salt as an activator (Examples 1 to 14), the reaction proceeds quickly even at room temperature and efficiency is good compared to a conventionally known case in which a small additive amount of a polar aprotic solvent is used (Comparative Examples 1 and 2).

Moreover, it can be seen from Table 2 that in an esterification reaction of a subsequent step, an acid chloride solution that is produced using at least 1.1 equivalents and not more than 3.0 equivalents of a polar aprotic solvent or a tetraalkylammonium salt provides good reaction results (Examples 15 to 28), whereas, in a case in which a small additive amount of a polar aprotic solvent is used, not only does the conversion rate decrease and the reaction fail to reach completion, the yield may also decrease. This is because a large amount of by-product production is observed in the reaction system (Comparative Examples 14 and 15).

Furthermore, it can be seen from Tables 1 and 2 that although good reaction results are obtained in a subsequent esterification reaction in a case in which a liquid separation operation is carried out to remove an oily liquid that is immiscible with a water-immiscible organic solvent after carrying out an acid chlorination reaction using at least 1.1 equivalents and not more than 3.0 equivalents of a polar aprotic solvent or tetraalkylammonium salt as an activator (Examples 1 to 28), the conversion rate significantly decreases, the reaction does not reach completion, and preferable results are not obtained if the esterification reaction is carried out in a state with an oily liquid present without carrying out a liquid separation operation (Comparative Examples 14 to 19 and 22 to 24). This is because a large amount of halogenating agent that causes side reactions remains in the reaction system. Moreover, it can be seen that in a case in which an esterification reaction is carried out in a state with an oily liquid being present in the acid chlorination reaction, even if an excess amount of triethylamine is used as a base, the produced amount of by-product increases, and thus preferable results are not obtained (Comparative Examples 20, 21, 25, and 26).

The invention claimed is:

1. A method of producing an acid halide solution comprising:
    a first step of reacting a dicarboxylic acid compound of formula (I), shown below,

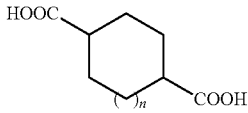

where n is 0 or 1, with a halogenating agent in a water-immiscible organic solvent in the presence of at least 1.1 molar equivalents and not more than 3.0 molar equivalents of an activator relative to the dicarboxylic acid compound of formula (I) to obtain a reaction liquid including a solution that contains an acid halide compound of formula (II), shown below,

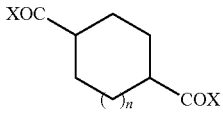

where n is 0 or 1 and X is a halogen atom, and an oily liquid that is immiscible with the solution; and
    a second step of removing the oily liquid from the reaction liquid obtained in the first step to obtain a purified liquid containing the acid halide compound of formula (II), wherein
    the activator is an amide solvent.

2. The method of producing an acid halide solution according to claim 1, wherein
    the amide solvent is at least one selected from the group consisting of N,N-dimethylformamide, N,N-dimethylacetamide, N-methylpyrrolidone, and 1,3-dimethyl-2-imidazolidinone.

3. A method of producing an acid halide solution comprising:
    a first step of reacting a dicarboxylic acid compound of formula (I), shown below,

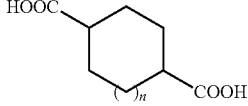

where n is 0 or 1, with a halogenating agent in a water-immiscible organic solvent in the presence of at least 1.1 molar equivalents and not more than 3.0 equivalents of an activator relative to the dicarboxylic acid compound of formula (I) to obtain a reaction liquid including a solution that contains an acid halide compound of formula (II), shown below,

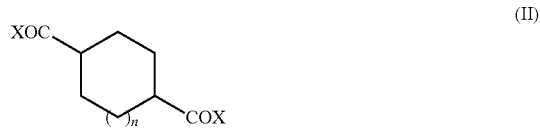

where n is 0 or 1 and X is a halogen atom, and an oily liquid that is immiscible with the solution; and
    a second step of removing the oily liquid from the reaction liquid obtained in the first step to obtain a purified liquid containing the acid halide compound of formula (II), wherein
    the activator is at least one selected from the group consisting of benzyltriethylammonium chloride, methyltrioctylammonium chloride, tetrabutylammonium chloride, and benzyltrimethylammonium chloride.

4. The method of producing an acid halide solution according to claim 1, wherein
    the halogenating agent is at least one selected from the group consisting of thionyl chloride, oxalyl chloride, sulfuryl chloride, phosphoryl chloride, phosphorus trichloride, and phosphorus pentachloride.

5. The method of producing an acid halide solution according to claim 1, wherein
    the acid halide compound of formula (II) is a dicarboxylic acid chloride of formula (II-1), shown below,

where n is 0 or 1.

6. A method of producing a monoester compound of formula (V), shown below,

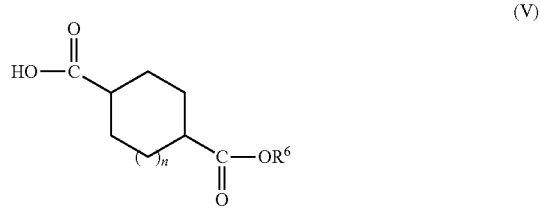

where $R^6$ is an organic group and n is 0 or 1, comprising
    a first step of reacting a dicarboxylic acid compound of formula (I), shown below,

where n is 0 or 1, with a halogenating agent in a water-immiscible organic solvent in the presence of at least 1.1 molar equivalents and not more than 3.0 molar equivalents of an activator relative to the dicarboxylic acid compound of formula (I) to obtain a reaction liquid including a solution that contains an acid halide compound of formula (II), shown below,

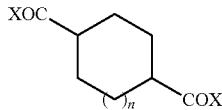
(II)

where n is 0 or 1 and X is a halogen atom, and an oily liquid that is immiscible with the solution;
a second step of removing the oily liquid from the reaction liquid obtained in the first step to obtain a purified liquid containing the acid halide compound of formula (II) and a fourth step of adding a hydroxy compound of formula (IV): R$^6$OH, where R$^6$ is the same as above, and a base to the purified liquid containing the acid halide compound of formula (II) obtained in the second step, wherein
the activator is an amide solvent or at least one selected from the group consisting of benzyltriethylammonium chloride, methyltrioctylammonium chloride, tetrabutylammonium chloride, and benzyltrimethylammonium chloride.

7. The method of producing a monoester compound according to claim 6, wherein
the hydroxy compound of formula (IV) is a compound of formula (IV-1), shown below,

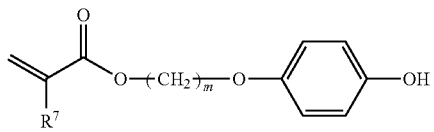
(IV-1)

where R$^7$ is a hydrogen atom, a methyl group, or a chlorine atom and m is an integer of at least 1 and not more than 20.

8. The method of producing a monoester compound according to claim 6, further comprising
a fifth step of, after the fourth step, washing a reaction liquid obtained through the fourth step with an aqueous solution having a pH of at least 5.0 and not higher than 6.0.

9. The method of producing a monoester compound according to claim 8, wherein
the aqueous solution having a pH of at least 5.0 and not higher than 6.0 is either or both of (1) an aqueous solution of a mixture of acetic acid and sodium acetate and (2) an aqueous solution of a mixture of potassium hydrogen phthalate and sodium hydroxide.

10. The method of producing an acid halide solution according to claim 1, further comprising a third step of, after the second step, concentrating the purified liquid obtained in the second step.

11. The method of producing an acid halide solution according to claim 1, wherein
the dicarboxylic acid compound of formula (I) is a compound of formula (I-a), shown below,

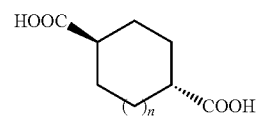
(I-a)

where n is 0 or 1.

12. The method of producing an acid halide solution according to claim 3, further comprising
a third step of, after the second step, concentrating the purified liquid obtained in the second step.

13. The method of producing an acid halide solution according to claim 3, wherein
the dicarboxylic acid compound of formula (I) is a compound of formula (I-a), shown below,

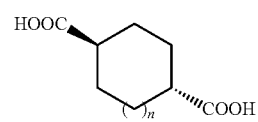
(I-a)

where n is 0 or 1.

14. The method of producing an acid halide solution according to claim 3, wherein
the halogenating agent is at least one selected from the group consisting of thionyl chloride, oxalyl chloride, sulfuryl chloride, phosphoryl chloride, phosphorus trichloride, and phosphorus pentachloride.

15. The method of producing an acid halide solution according to claim 3, wherein
the acid halide compound of formula (II) is a dicarboxylic acid chloride of formula (II-1), shown below,

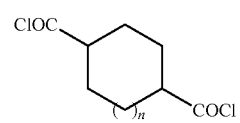
(II-1)

where n is 0 or 1.

* * * * *